United States Patent
Bond et al.

(10) Patent No.: US 9,234,794 B2
(45) Date of Patent: Jan. 12, 2016

(54) FIBER OPTIC COUPLED MULTIPASS GAS MINICELL, DESIGN ASSEMBLY THEREOF

(71) Applicant: Lawrence Livermore National Security, LLC, Livewrmore, CA (US)

(72) Inventors: Tiziana C. Bond, Livermore, CA (US); Mihail Bora, Livermore, CA (US); Michael A. Engel, Ripon, CA (US); James F. McCarrick, Dublin, CA (US); Bryan D. Moran, Pleasanton, CA (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 5 days.

(21) Appl. No.: 14/311,616

(22) Filed: Jun. 23, 2014

(65) Prior Publication Data

US 2015/0316412 A1    Nov. 5, 2015

Related U.S. Application Data

(60) Provisional application No. 61/839,265, filed on Jun. 25, 2013.

(51) Int. Cl.
| | | |
|---|---|---|
| G01N 21/00 | (2006.01) | |
| G01N 21/59 | (2006.01) | |
| G01J 3/02 | (2006.01) | |
| G01J 3/10 | (2006.01) | |
| G01J 3/42 | (2006.01) | |
| G01N 21/03 | (2006.01) | |

(52) U.S. Cl.
CPC .............. *G01J 3/0218* (2013.01); *G01J 3/10* (2013.01); *G01J 3/42* (2013.01); *G01J 2003/421* (2013.01); *G01N 21/03* (2013.01)

(58) Field of Classification Search
USPC .................................. 356/432–437, 246, 440
See application file for complete search history.

(56) References Cited

U.S. PATENT DOCUMENTS

| 5,521,703 | A | * | 5/1996 | Mitchell | G01N 21/65 356/301 |
|---|---|---|---|---|---|
| 6,040,915 | A | * | 3/2000 | Wu | G01N 21/3504 250/345 |
| 6,137,576 | A | * | 10/2000 | Pauluth | G01N 21/45 356/477 |
| 6,275,288 | B1 | * | 8/2001 | Atkinson | G01N 21/39 250/339.13 |
| 6,678,052 | B1 | * | 1/2004 | Hanagandi | G01N 21/85 356/410 |
| 8,309,929 | B2 | | 11/2012 | Bond et al. | |
| 2004/0004720 | A1 | * | 1/2004 | Cliche | G01N 21/03 356/440 |
| 2006/0092423 | A1 | * | 5/2006 | Servaites | G01N 21/359 356/437 |
| 2008/0231857 | A1 | * | 9/2008 | Depeursinge | A61B 5/14552 356/437 |
| 2010/0002231 | A1 | * | 1/2010 | Chindo | H03L 7/26 356/370 |
| 2012/0287418 | A1 | * | 11/2012 | Scherer | G01N 21/61 356/51 |
| 2012/0330568 | A1 | * | 12/2012 | Izawa | G01N 21/0303 702/24 |
| 2013/0135619 | A1 | * | 5/2013 | Hirata | G01N 21/39 356/409 |

* cited by examiner

*Primary Examiner* — Sang Nguyen
(74) *Attorney, Agent, or Firm* — Eddie E. Scott

(57) ABSTRACT

A method directs a gas of interest into a minicell and uses an emitting laser to produce laser emission light that is directed into the minicell and onto the gas of interest. The laser emission light is reflected within the cell to make multipasses through the gas of interest. After the multipasses through the gas of interest the laser light is analyzed to produces gas spectroscopy data. The minicell receives the gas of interest and a transmitting optic connected to the minicell that directs a beam into the minicell and onto the gas of interest. A receiving optic connected to the minicell receives the beam from the gas of interest and directs the beam to an analyzer that produces gas spectroscopy data.

23 Claims, 5 Drawing Sheets

FIBER OPTIC COUPLED MULTIPASS GAS MINICELL, DESIGN ASSEMBLY THEREOF

CROSS-REFERENCE TO RELATED APPLICATIONS

This application claims priority to and benefit under 35 U.S.C. §119(e) of U.S. Provisional Patent Application No. 61/839,265 filed Jun. 25, 2013 entitled "Fiber optic coupled multipass gas minicell, design assembly thereof," the content of which is hereby incorporated by reference in its entirety for all purposes.

STATEMENT AS TO RIGHTS TO APPLICATIONS MADE UNDER FEDERALLY SPONSORED RESEARCH AND DEVELOPMENT

The United States Government has rights in this application pursuant to Contract No. DE-AC52-07NA27344 between the United States Department of Energy and Lawrence Livermore National Security, LLC for the operation of Lawrence Livermore National Laboratory.

BACKGROUND

1. Field of Endeavor

The present application relates to gas spectroscopy and more particularly to a fiber optic coupled multipass gas minicell.

2. State of Technology

This section provides background information related to the present disclosure which is not necessarily prior art.

U.S. Pat. No. 8,309,929 for tunable photonic cavities for in-situ spectroscopic trace gas detection includes the following information: "Gas analysis is conventionally performed using laboratory analytical techniques, e.g., gas chromatography or mass spectrometry (GC-MS), which do not satisfy current device and material constraints for unattended, flexible ground sensors, or for lightweight, highly sensitive systems for avionic operations. Absorption spectroscopy is a powerful alternative approach for gas in-field detection and identification, and several interesting techniques have been developed including tunable diode laser absorption spectroscopy (TDLAS). Typically, this occurs in the infrared (IR) region of the spectrum. Recently, micromechanically tunable vertical-cavity surface-emitting lasers (VCSELs) have been implemented in such fashion for near infrared (NIR) spectroscopy. Unfortunately, many existing TDLAS systems exhibit drawbacks that limit their deployment, including the need for cryogenic cooling, a requirement for a bulky multipass cell, or a long hollow or porous fiber with a relatively slow time response."

Tunable Absorption Spectroscopy is a common technique for gas detection and simply provides the chemical fingerprint of components by the absorption of the light at the wavelengths which resonate with the molecules inducing vibrations and rotations. By simply shining light through a volumetric gas sample on a detector, when the wavelengths is right, quench will occur and a dip in the power will be recorded at the detector.

In order to improve sensitivity various approaches are taken, from increasing the number of passes of light through the volume (thus increasing the absorption in discrete defined spaces) to implementing modulation techniques to remove background and noise.

Applicants have developed an extremely small and robust cell in which a very small volumes of gas is sampled while maintaining high sensitivity and specificity by combining it with highly tunable VCSELs (to provide various absorption lines of one specie and capture varies elements at once) and wavelength modulation spectroscopy (to extract high harmonics which are not affected by the 1/f noise).

SUMMARY

Features and advantages of the disclosed apparatus, systems, and methods will become apparent from the following description. Applicant is providing this description, which includes drawings and examples of specific embodiments, to give a broad representation of the apparatus, systems, and methods. Various changes and modifications within the spirit and scope of the application will become apparent to those skilled in the art from this description and by practice of the apparatus, systems, and methods. The scope of the apparatus, systems, and methods is not intended to be limited to the particular forms disclosed and the application covers all modifications, equivalents, and alternatives falling within the spirit and scope of the apparatus, systems, and methods as defined by the claims.

The disclosed apparatus, systems, and methods provide an all-optical as well as wireless compatible gas cell with an extremely small footprint for the sensitive detection of multiple gases in small, inaccessible volumes or extreme, impervious conditions. The disclosed apparatus, systems, and methods have use in the detection and quantification of multiple gases in small footprint with low power requirements and high sensitivity/selectivity. The disclosed apparatus, systems, and methods have use in the defense, energy, and environmental departments and in industry. The disclosed apparatus, systems, and methods can be used to certify exhaust compliances, provide pollution controls, monitor aircraft headspace atmospheric balances and aging of closed systems, enable forensic analysis in either CBRN global threats or local law enforcements in drug/alcohol screenings, and assisting agronomic/rural developments.

In one or more embodiments the disclosed apparatus and systems comprise a cell that receives a gas of interest, a transmitting optic connected to the cell that directs a light beam into the cell and the gas of interest, a receiving optic connected to the cell that receives the light beam from the gas of interest; and an analyzer connected to the receiving optic that produces gas spectroscopy data.

In one or more embodiments the disclosed system and methods comprise a method for analyzing a gas of interest using a cell by directing the gas of interest into the cell, using one or more emitting lasers to produce laser emission light, directing the laser emission light into the cell and the gas of interest, reflecting the laser emission light within the cell to make multiple passes through the gas of interest, and analyzing the laser emission light after the multiple passes through the gas of interest to produces gas spectroscopy data.

The disclosed apparatus, systems, and methods are not limited to either one gas or one kind of laser source and the disclosed apparatus, systems, and methods are wide open to various configurations.

The apparatus, systems, and methods are susceptible to modifications and alternative forms. Specific embodiments are shown by way of example. It is to be understood that the apparatus, systems, and methods are not limited to the particular forms disclosed. The apparatus, systems, and methods cover all modifications, equivalents, and alternatives falling within the spirit and scope of the application as defined by the claims.

BRIEF DESCRIPTION OF THE DRAWINGS

The accompanying drawings, which are incorporated into and constitute a part of the specification, illustrate specific embodiments of the apparatus, systems, and methods and, together with the general description given above, and the detailed description of the specific embodiments, serve to explain the principles of the apparatus, systems, and methods.

DETAILED DESCRIPTION OF SPECIFIC EMBODIMENTS

Figure 2:
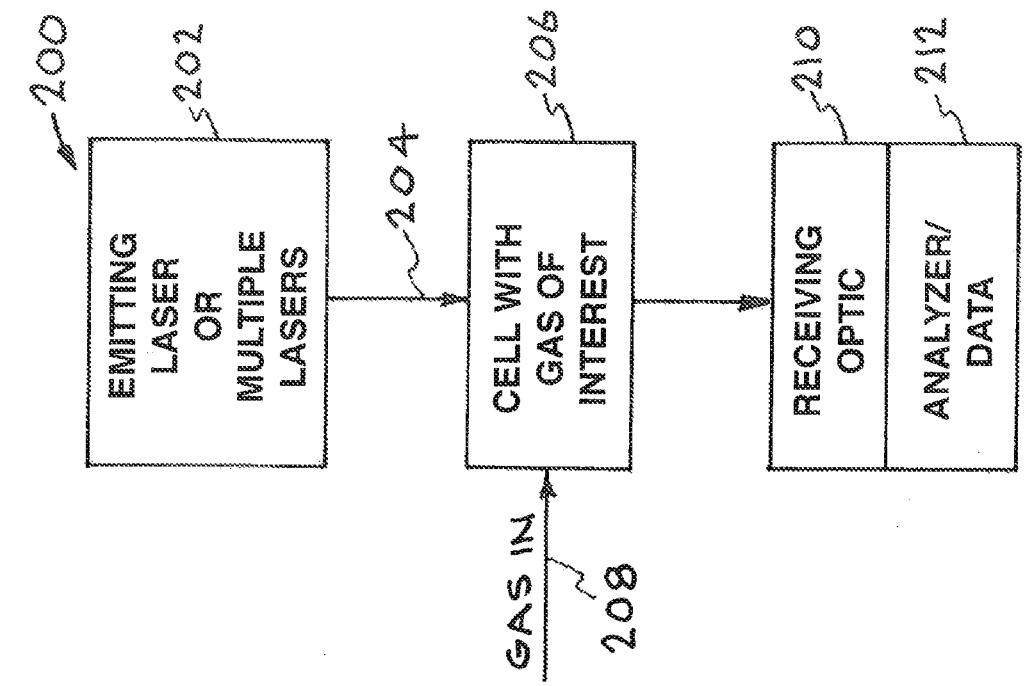
FIG. 2 is a flow chart illustrating another embodiment of Applicant's method of gas spectroscopy of a gas of interest.

Referring to the drawings, to the following detailed description, and to incorporated materials, detailed information about the apparatus, systems, and methods is provided including the description of specific embodiments. The detailed description serves to explain the principles of the apparatus, systems, and methods. The apparatus, systems, and methods are susceptible to modifications and alternative forms. The application is not limited to the particular forms disclosed. The application covers all modifications, equivalents, and alternatives falling within the spirit and scope of the apparatus, systems, and methods as defined by the claims.

Figure 1:
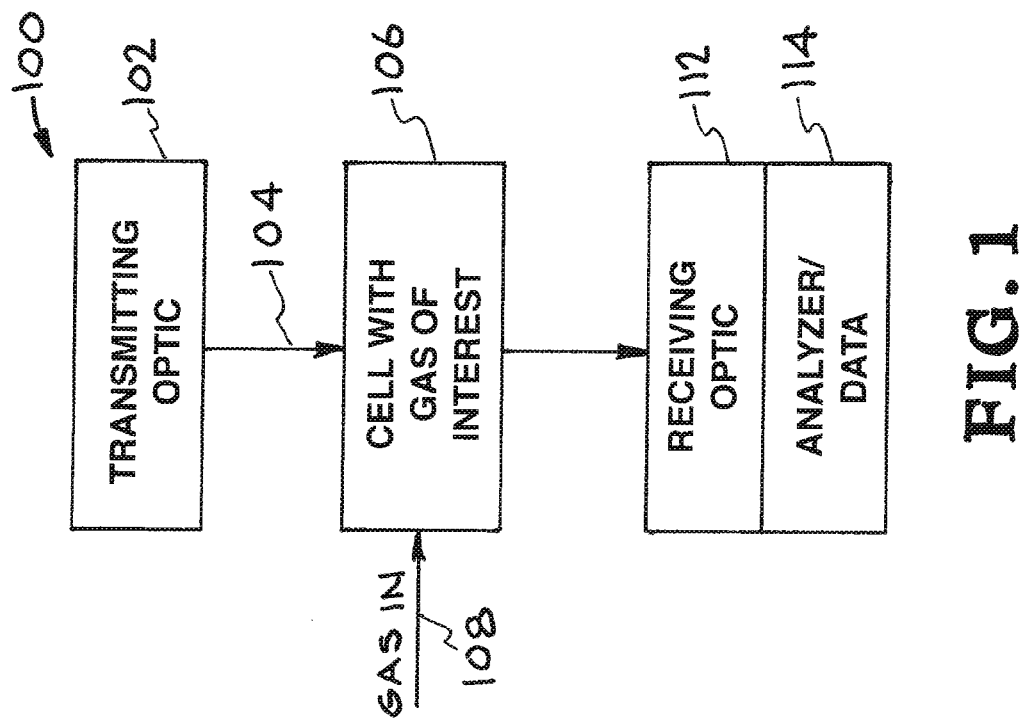
FIG. 1 is a flow chart illustrating one embodiment of Applicant's method of gas spectroscopy of a gas of interest.

Referring now to the drawings and in particular to FIG. 1, a flow chart illustrates one embodiment of Applicant's method of gas spectroscopy of a gas of interest. The method is designated generally by the reference numeral 100. The method 100 is a method of analyzing a gas of interest using a cell by directing the gases of interest into the cell, using one or more emitting light sources to produce emission light, directing the emission light into the cell and the gas of interest, reflecting the emission light within the cell to travel multiple passes through the gas of interest, and analyzing the emission light after the multipasses through the gas of interest to produce gas spectroscopy data.

In the method 100 a transmitting optic 102 funnels a light beam 104 that is directed into a minicell 106. The gas of interest 108 is introduced into the minicell 106. A receiving optic 112 connected to the minicell 106 receives the light beam 104 through a fiber 110 from the minicell 106 after the light beam 104 passes through the gas of interest 108. The light beam 104 that has passed through the gas of interest 108 is directed to the receiving optic 112 and an analyzer 114 connected to the receiving optic 112. The analyzer produces gas spectroscopy data for the gas of interest.

Referring now to FIG. 2, a flow chart illustrates another embodiment of Applicant's method of gas spectroscopy of a gas of interest. This embodiment of the method is designated generally by the reference numeral 200. The method 200 is a method of analyzing a gas of interest using a cell by directing the gas of interest into the cell, using one or more emitting lasers to produce emission light, directing the emission light into the cell and the gas of interest, reflecting the emission light within the cell to make multipasses through the gas of interest, and analyzing the emission light after the multipasses through the gas of interest to produce gas spectroscopy data.

In the method 200 an emitting laser or multiple lasers 202 generate a laser beam 204 that is directed into a minicell 206. The gas of interest 208 is introduced into the minicell 206. A receiving optic 210 connected to the minicell 206 receives the beam 204 from the minicell 206 through fiber 214 after the beam 204 passes through the gas of interest 208. The beam 204 that has passed through the gas of interest 208 is directed to the receiving optic 210 and an analyzer 212 connected to the receiving optic 210. The analyzer produces gas spectroscopy data.

Miniaturized Gas Spectrometer & Multipass Minicell

Applicants have developed a miniaturized gas spectrometer with a small footprint. The miniaturized gas spectrometer utilizes a multipass minicell. Applicants miniaturized gas spectrometer provides an all-optical as well as wireless compatible gas cell with an extremely small footprint for the sensitive detection of multiple gases in small, inaccessible volumes or extreme, impervious conditions. Applicants miniaturized gas spectrometer has use in the detection and quantification of multiple gases in small footprint with low power requirements and high sensitivity/selectivity. The apparatus, systems, and methods have use in the defense, energy, and environmental departments and in industry. The apparatus, systems, and methods can be used to certify exhaust compliances, provide pollution controls, monitor aircraft headspace atmospheric balances and aging of closed systems, enable forensic analysis in either CBRN global threats or local law enforcements in drug/alcohol screenings, and assisting agronomic/rural developments.

Applicants have developed a miniaturized gas spectrometer with a small footprint that can be deployed in the overhead space of weapon systems and can continuously monitor surrounding gas composition. Current gas detection systems such as Fourier Transform Infrared (FTIR) spectrometers operate in a wide infrared region of the spectrum (2-20 μm), where most gases have a significant electrical dipole moment and have a strong absorption cross-section and signature. Most FTIR systems are large bench top instruments, making them unusable for the desired application.

Instead of performing spectroscopy over the entire infrared spectrum, Applicants select a miniaturized light source, i.e. a vertical cavity surface emitting laser or VCSEL that can be tuned over a narrower spectral range. By selecting the appropriate laser tuning range such that it covers several absorption lines for the species of interest, measurements can be performed on the composition of the analyzed gas. A wider variety of gas species can be measured if the approach is extended to an array of light of VCSELs, each with a different tuning range target. The multiplexed system would therefore allow a potentially significant reduction on the instrument footprint compared to traditional FTIR instrumentation.

In order to increase the sensitivity of the detection method a multipass White cell that has a total of 27 passes for an effective length of 2.5 m can be used. Applicants efforts were also been directed toward designing and fabricating a flow cell of size 4×5×1 cm3 by adjusting the mirror sizes and positions in the optical multipass cell.

Detection and identification of gas species using tunable laser diode laser absorption spectroscopy has been performed using Vertical Cavity Surface Emitting Lasers (VCSEL). Two detection methods were compared: direct absorbance and wavelength modulation spectroscopy (WMS). In the former, the output of a DC-based laser is directly monitored to detect any power quenching at the targeted specie absorption wavelength. In the latter, the emission wavelength of the laser is modulated by applying a sinusoidal component on the drive current of frequency ω, and measuring the harmonics component (2ω) of the photo-detected current. This method shows a better sensitivity measured as signal to noise ratio, and is less susceptible to interference effects such as scattering or fouling. Gas detection was initially performed at room temperature and atmospheric conditions using VCSELs of emission wavelength 763 nm for oxygen and 1392 nm for water, scanning over a range of approximately 10 nm, sufficient to cover 5-10 gas specific absorption lines that enable identification and quantization of gas composition. The amplitude and frequency modulation parameters were optimized for each detected gas species, by performing two dimensional sweeps for both tuning the bias current and either amplitude or frequency, respectively. Applicants found that the highest detected signal is observed for a wavelength modulation amplitude equal to the width of the gas absorbance lines, in good agreement with theoretical calculations, and for modulation frequencies below the time response of the lasers (<50 KHz). Applicants can easily achieve 100 ppm limit of detection (LOD) for O2 and CO2, and Applicants have been just limited by the current instrumentation.

Additional LOD studies and further implementation and packaging of VCSELs in diode arrays for continuous and simultaneous monitoring of multiple species in gaseous mixtures were conducted. Applicants pursued a two-prong approach: the first focused on the design, fabrication and characterization of MEMS-tunable long-wavelength VCSELs which allows flexibility and tunability; the second based on using commercial current-tunable VCSELs that despite a smaller tuning range are adequate to prove different single (and time-interleaved multiple) gas detection and can be potentially assembled for synchronous multiplexed detection with a small form factor given their compact package.

Applicants previous experiments were run in standard atmospheric condition and targeted species have been oxygen, water vapors and carbon dioxide, present at relatively high concentrations. A second set of experiments on the gas absorption based detection were performed with a multipass White gas cell, and for the third one multiple VCSELS were integrated on a printed circuit board (further reduced in size and optimized) and both water and oxygen were detected at the same time by running each laser diode in a sequential manner.

In order to implement and assess performance of the sensors at various concentration levels Applicants have assembled a computer controlled system capable of delivering gases and volatile compounds in a flow chamber at concentrations of 100s of ppm and higher.

Example 1

Figure 3:
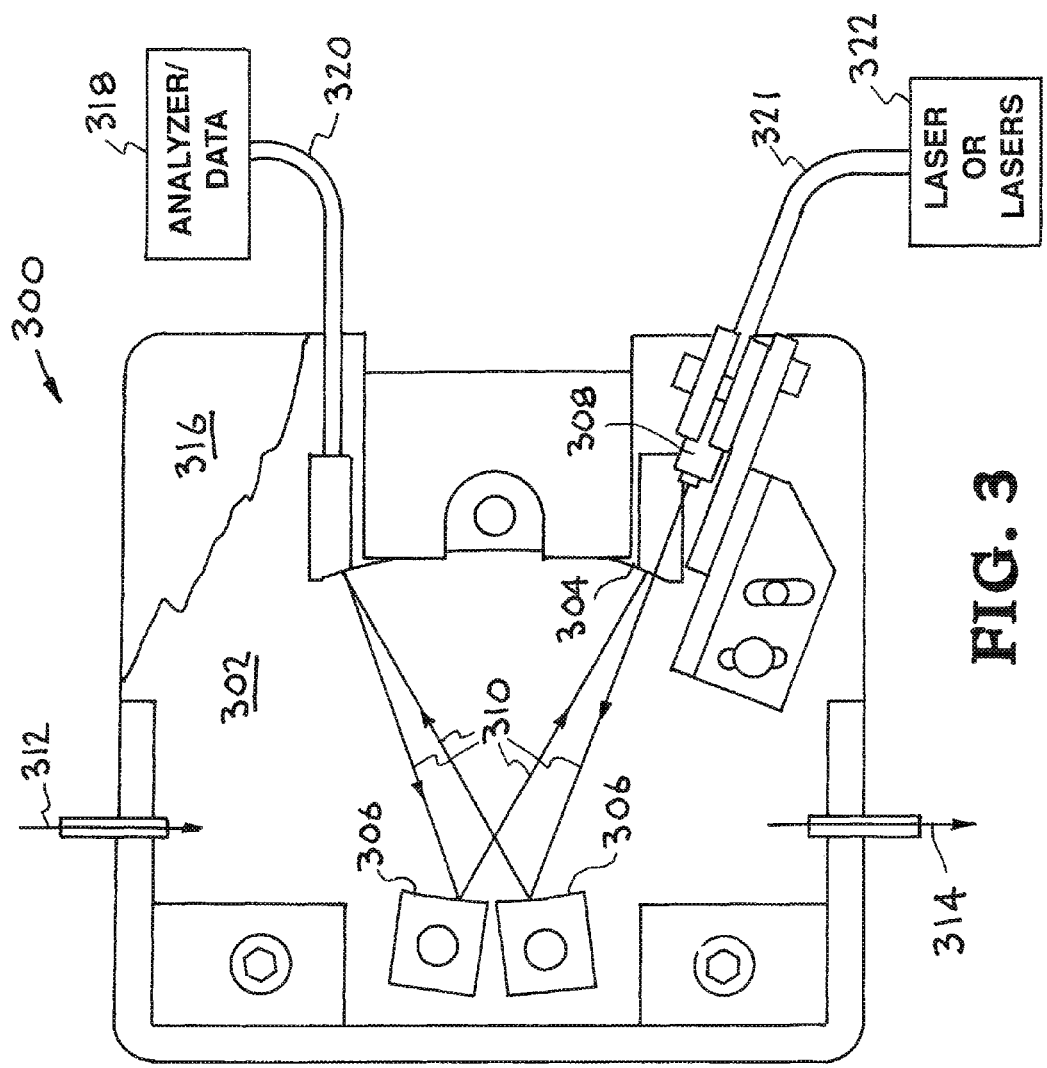
FIG. 3 illustrates an example of one embodiment of Applicant's minicell apparatus and system for gas spectroscopy of a gas of interest.

Referring now to FIG. 3, a first example of one embodiment of Applicant's minicell apparatus and system for gas spectroscopy of a gas of interest is illustrated. The minicell is designated generally by the reference numeral 300. The minicell 300 is a multipass White cell that has a total of 64 passes for an effective length of 1.6 m, in a footprint of 4×5×1 cm$^3$. The minicell 300 includes an inlet 312 and an outlet 314 for introducing and removing the gas of interest into the interior 302 of the minicell 300. The example 1 minicell 300 includes a cover 316 that confines the gas of interest within the interior 302 of the minicell.

A laser (or array of lasers) 322 produces a laser beam that is carried by the optical fiber 321 and directed into the minicell 300. A first set of mirrors 306 and an opposing mirror 304 are positioned to reflect the laser beam 310 so that it makes multipasses through the interior 302 of the minicell 300. The mirrors 306 and the mirror 304 are accurately positioned so that the reflected laser beam 310 makes twenty seven (27) passes through the interior 302 of the minicell 300 and through the gas of interest within the minicell 300. On the last pass the laser beam 310 exits the minicell 300 through the optical fiber 320 and is directed to the analyzer 318.

The structural details of the minicell 300 having been described the operation of the operation of the minicell apparatus and system 300 for gas spectroscopy of a gas of interest will be considered. The multi-pass cell 300 is composed of the sets of mirrors 304 and 306. The two mirrors on the side have their inclination offset from each other and help steer the beam 310 inside the cavity 302. The opposing mirror has two notches cut in to allow the entrance and exit beams inside the cell. Applicants control the intensity of the laser beam right at the surface of the mirrors. Because the output of the laser diode is divergent with an opening of about 20 degrees the beam steering mirrors are filled completely. The optical focal length of the mirrors is chosen as a 1:1 relay imaging system, such that the beams are focused on the entrance/exit mirror to avoid chopping the beam at the edges and hence losing signal, while also allowing a higher number of passes.

Detection and identification of gas species using tunable laser diode laser absorption spectroscopy is performed using Vertical Cavity Surface Emitting Lasers (VCSEL). Two detection methods can be utilized: direct absorbance and wavelength modulation spectroscopy (WMS). In the former, the output of a DC-based laser is directly monitored to detect any power quenching at the targeted specie absorption wavelength. In the latter, the emission wavelength of the laser is modulated by applying a sinusoidal component on the drive current of frequency ω, and measuring the harmonics component (2ω) of the photo-detected current. This method shows a better sensitivity measured as signal to noise ratio, and is less susceptible to interference effects such as scattering or fouling. Gas detection was initially performed at room temperature in a previous embodiment and atmospheric conditions using VCSELs of emission wavelength 763 nm for oxygen and 1392 nm for water, scanning over a range of approximately 10 nm, sufficient to cover 5-10 gas specific absorption lines that enable identification and quantization of gas composition. The amplitude and frequency modulation parameters were optimized for each detected gas species, by performing two dimensional sweeps for both tuning the bias current and either amplitude or frequency, respectively.

Example 2

Figure 4:
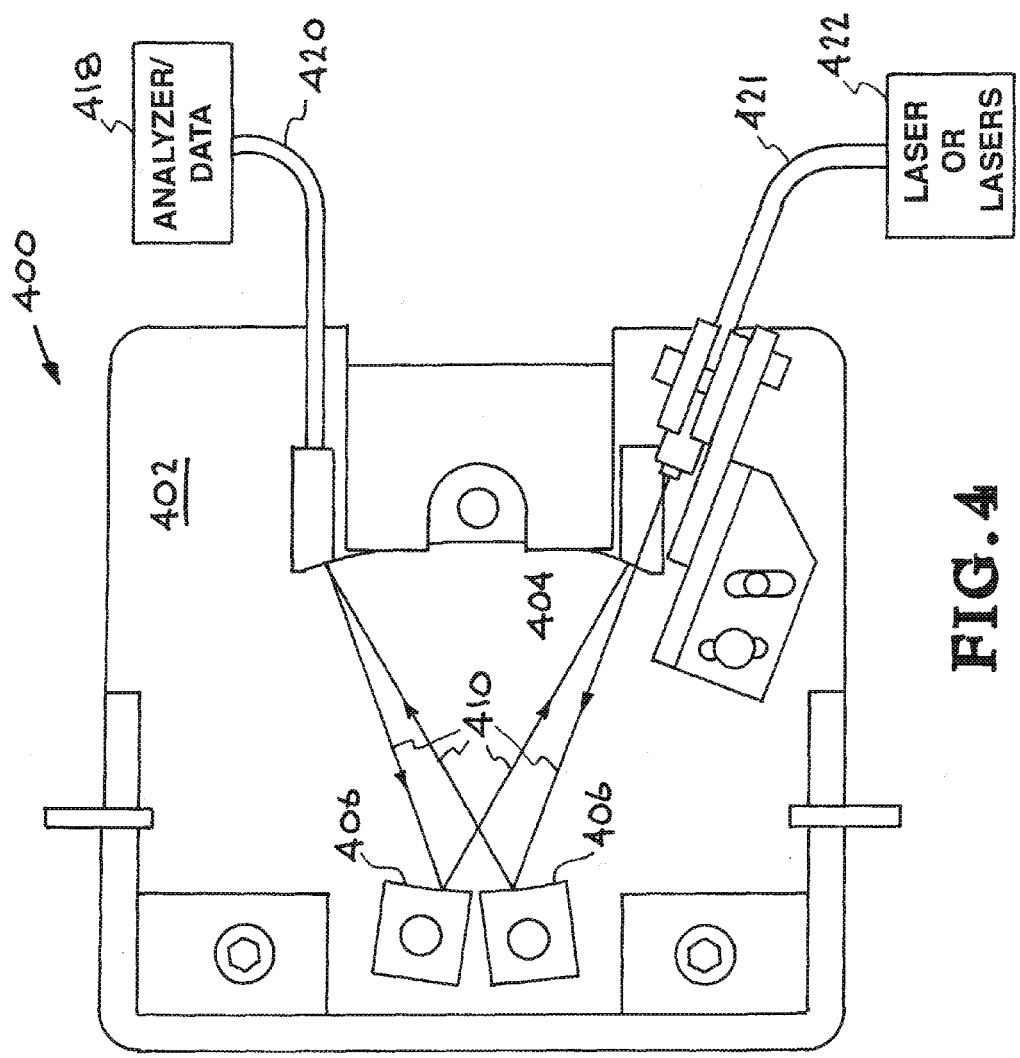
FIG. 4 illustrates another example of one embodiment of Applicant's minicell apparatus and system for gas spectroscopy of a gas of interest.

Referring now to FIG. 4, a second example of an embodiment of Applicant's minicell apparatus and system for gas spectroscopy of a gas of interest is illustrated. This embodiment of the minicell is designated generally by the reference numeral 400. The minicell 400 is a multipass White cell that has a total of 64 passes for an effective length of 1.6 m, in a footprint of 5×4×1 cm$^3$. The example 2 minicell 400 does not include the cover of the minicell 300 shown in FIG. 3. Instead the interior 402 of the minicell 400 is open to the ambient atmosphere or the gas of interest being sampled.

A laser (or array of lasers) 422 produces a laser beam that is carried by the optical fiber 421 and directed into the minicell 400. A first set of mirrors 406 and an opposing mirror 404 are positioned to reflect the laser beam 410 so that it makes multipasses through the interior 402 of the minicell 400. The mirrors 406 and the mirror 404 are accurately positioned so that the reflected laser beam 410 makes twenty seven (27) passes through the interior 402 of the minicell 400 and through the ambient atmosphere or the gas of interest that is within the interior 402 of the minicell 400. On the last pass the laser beam 410 exits the minicell 400 through the optical fiber 420 and is directed to the analyzer 418.

Example 3

Multiplexing

Figure 5:
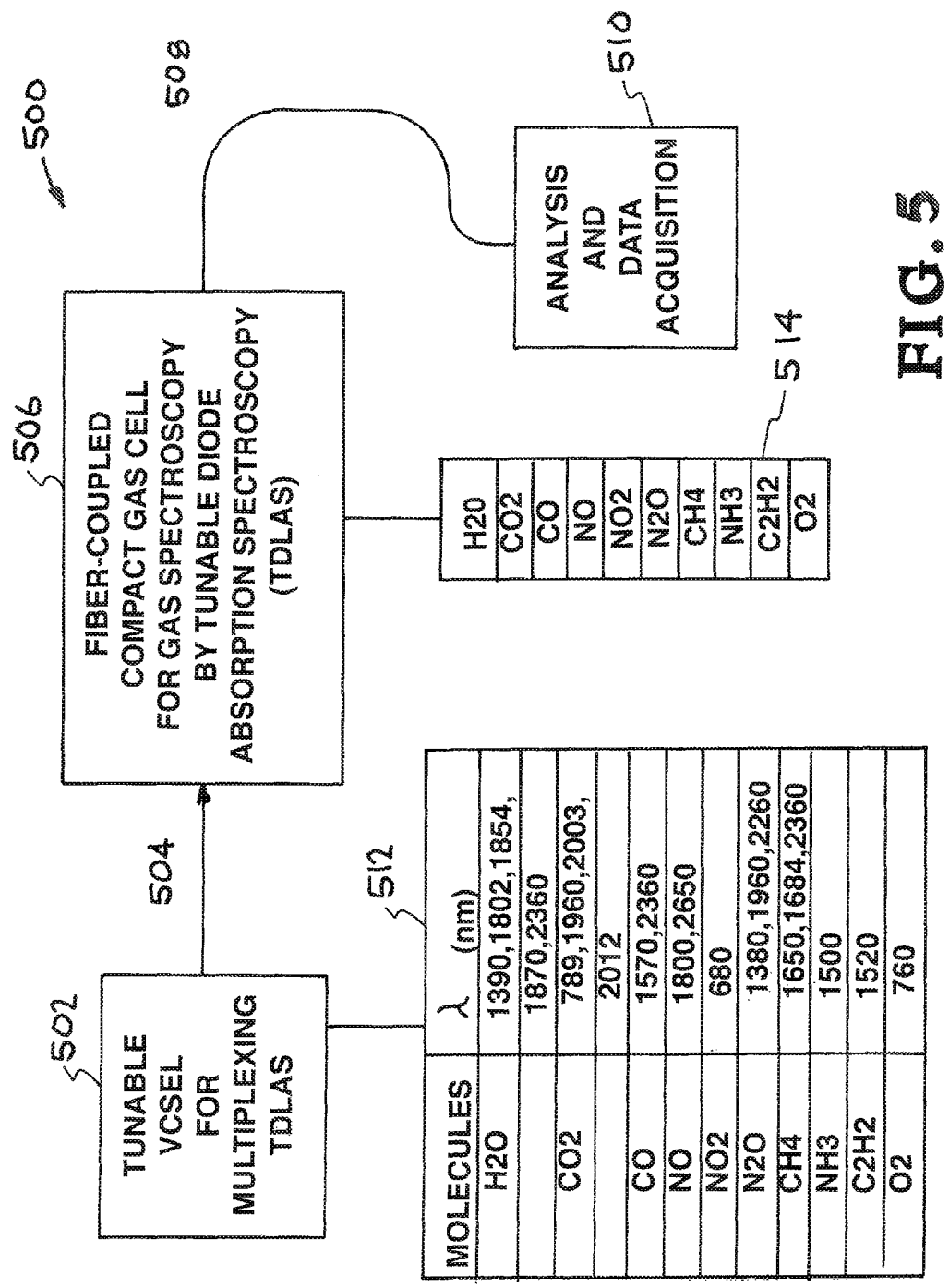
FIG. 5 illustrates another example of an embodiment of Applicant's minicell apparatus and system for multiplexing Tunable Laser Diode Absorption Spectroscopy (TDLAS).

Referring now to FIG. 5, a third example embodiment of Applicant's minicell apparatus and system for gas spectroscopy of a gas of interest is illustrated. The system is designated generally by the reference numeral 500. The system 500 utilizes multiplexing Tunable Laser Diode Absorption Spectroscopy (TDLAS).

As illustrated in FIG. 5, a tunable Vertical Cavity Surface Emitting Laser (VCSEL) 502 produces a beam that is directed through an optical fiber 504 to a minicell 506. The minicell 506 is a fiber-coupled compact gas cell for gas spectroscopy by tunable diode absorption spectroscopy. The beam passes through the gas of interest in the minicell 506 and is directed to an analysis and data acquisition unit 510 through optical fiber 508.

The table 512 in FIG. 5 identifies various molecules and their associated detection wavelength. The tunable Vertical Cavity Surface Emitting Laser (VCSEL) 502 produces a beam that includes all of the identified wavelengths for the identified gases. The fiber-coupled compact gas cell for gas spectroscopy by tunable diode absorption spectroscopy minicell 506 identifies the gases listed in the table 514.

Example 4

Wireless Controls

Figure 6:
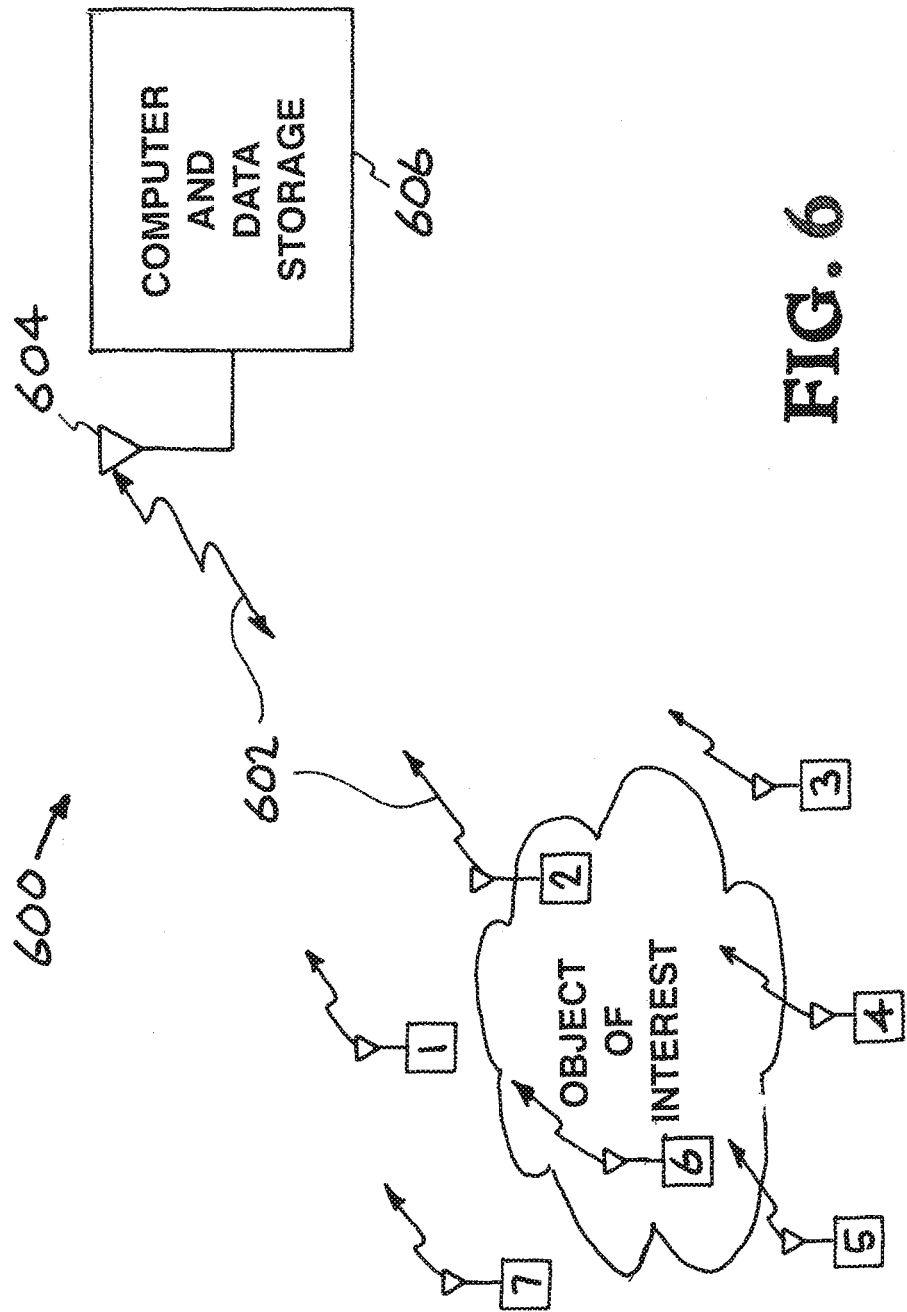
FIG. 6 illustrates another example of an embodiment of Applicant's minicell apparatus and system using wireless controls for multiple minicells.

Referring now to FIG. 6, a fourth example embodiment of Applicant's minicell apparatus and system for gas spectroscopy of a gas of interest is illustrated. The system is designated generally by the reference numeral 600. The system 600 provides wireless controls for multiple minicells. Each minicell is connected to a wireless board that sends data signals for the gas of interest detected by the particular minicell.

Seven individual wireless minicell units are illustrated in FIG. 6. The individual wireless minicell units are identified by the reference numerals 1 through 7. Each of the individual wireless minicell units sends and receives a data signal. A computer and data storage unit 606 unit includes an antenna 604 for receiving and sending the data signals 602.

Mirrors & Mirror Arrangement

Additional example embodiments of Applicant's minicell apparatus and system for gas spectroscopy of a gas of interest will be considered with particular emphasis on the mirrors and mirror arrangement. One example embodiment will be described using the minicell 300 illustrated in drawing FIG. 3. This example embodiment is a minicell representing the scaling of the cell: path length per unit volume: L (cm)/V (cm$^3$). The cell 300 is optimized to obtain the highest FoM equa to 160 cm/(4×5×1) cm$^3$=8 cm-2 when considering the whole cell assembly. If only the volume of the interrogated gas (between the mirrors) is considered the FoM<42=160 cm/(2.5×2.5×0.6) cm$^3$ where 2.5 cm is the distance between the mirrors and (2.5×0.6) cm2 is the area of the bigger T-shaped mirror which is an overestimate of the interrogated effective area.

The mirrors 304 and 306 are cut in particular shape and size to enable the compact reflection. Light enters through optical fiber 308 and is launched onto the mirror 306 through the angled fiber input 308. The light is reimaged on the T-mirror 304 at each of the 64 passes and exits through the angled fiber-coupled detector port and optical fiber 320 on side of T-mirror 304. This provides an optical path of 1.6 m folded over 2.5 cm physical length (64 paths) with transmission~10-50% (=0.6-2 um).

Although the description above contains many details and specifics, these should not be construed as limiting the scope of the application but as merely providing illustrations of some of the presently preferred embodiments of the apparatus, systems, and methods. Other implementations, enhancements and variations can be made based on what is described and illustrated in this patent document. The features of the embodiments described herein may be combined in all possible combinations of methods, apparatus, modules, systems, and computer program products. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination. Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described above should not be understood as requiring such separation in all embodiments.

Therefore, it will be appreciated that the scope of the present application fully encompasses other embodiments which may become obvious to those skilled in the art. In the claims, reference to an element in the singular is not intended to mean "one and only one" unless explicitly so stated, but rather "one or more." All structural and functional equivalents to the elements of the above-described preferred embodiment that are known to those of ordinary skill in the art are expressly incorporated herein by reference and are intended to be encompassed by the present claims. Moreover, it is not necessary for a device to address each and every problem sought to be solved by the present apparatus, systems, and methods, for it to be encompassed by the present claims. Furthermore, no element or component in the present disclosure is intended to be dedicated to the public regardless of whether the element or component is explicitly recited in the claims. No claim element herein is to be construed under the provisions of 35 U.S.C. 112, sixth paragraph, unless the element is expressly recited using the phrase "means for."

While the apparatus, systems, and methods may be susceptible to various modifications and alternative forms, specific embodiments have been shown by way of example in the drawings and have been described in detail herein. However, it should be understood that the application is not intended to be limited to the particular forms disclosed. Rather, the application is to cover all modifications, equivalents, and alternatives falling within the spirit and scope of the application as defined by the following appended claims.

The invention claimed is:

1. An apparatus for gas spectroscopy of a gas of interest, comprising:
    a gas cell, said gas cell including
    a first side,
    a second side, and
    an interior,
    wherein said second side is opposed to said first side and wherein said interior is between said first side and said second side,
    a first side mirror positioned in said interior adjacent said first side,
    a second side mirror positioned in said interior adjacent said second side,
    wherein said second side mirror is opposed to said first side mirror with said interior between said first side mirror and said second side mirror,
    a gas containment system for introducing the gas of interest into said interior of said gas cell between said first side mirror and said second side mirror,
    a light source that produces a light beam,
    a transmitting optical fiber connected to said gas cell that receives said light beam from said light source and directs said light beam into said interior of said gas cell between said first side mirror and said second side mirror and onto the gas of interest in said interior of said gas cell between said first side mirror and said second side mirror,
    wherein said first side mirror and said second side mirror are positioned relative to each other so that said light beam is reflected between said first side mirror and said second side mirror through the gas of interest in said interior of said gas cell,
    a receiving optical fiber connected to said gas cell, said optical fiber positioned relative to said first side mirror and said second side mirror so that said optical fiber receives said light beam from the gas of interest in said interior of said gas cell and provides an exit light beam; and
    a gas spectroscopy analyzer connected to said receiving optical fiber that receives said exit light beam and produces gas spectroscopy data.

2. The apparatus for gas spectroscopy of a gas of interest of claim 1 wherein said first side mirror and said second side mirror in said interior of said gas cell are arranged to reflect said light beam from said first side mirror to said second side mirror so that said light beam makes a multiplicity of different passes through said gas of interest in said interior of said gas cell and wherein said first side mirror has an inclination that steers said light beam to completely fill said second side mirror so that said light beam makes a multiplicity of different passes through said gas of interest in said interior of said gas cell.

3. The apparatus for gas spectroscopy of a gas of interest of claim 1 wherein said first side mirror and said second side mirror are arranged to reflect said light beam from said first side mirror to said second side mirror so that said light beam makes a multiplicity of different passes through said gas of interest in said interior of said gas cell and wherein said first side mirror has an inclination that steers said light beam to completely fill said second side mirror so that said light beam makes a multiplicity of sixty-four different passes through the gas of interest.

4. The apparatus for gas spectroscopy of a gas of interest of claim 1 wherein said gas containment system includes an inlet into said gas cell and a conduit for directing the gas of interest into said gas cell.

5. The apparatus for gas spectroscopy of a gas of interest of claim 1 wherein said gas cell is a minicell having dimensions of four centimeters by five centimeters by one centimeter or less.

6. The apparatus for gas spectroscopy of a gas of interest of claim 1 wherein said first side mirror has a notch that direct said light beam to said receiving optical fiber.

7. The apparatus for gas spectroscopy of a gas of interest of claim 1 wherein said light source is a laser light source that produces said light beam.

8. The apparatus for gas spectroscopy of a gas of interest of claim 7 wherein said laser light source is a tunable laser.

9. The apparatus for gas spectroscopy of a gas of interest of claim 7 wherein said laser light source is a tunable diode laser.

10. The apparatus for gas spectroscopy of a gas of interest of claim 7 wherein said laser light source is a multiplicity of individual lasers.

11. The apparatus for gas spectroscopy of a gas of interest of claim 7 wherein said laser light source is a tunable vertical cavity surface emitting laser for multiplexing by providing laser light with wavelengths for multiple gases of interest.

12. The apparatus for gas spectroscopy of a gas of interest of claim 1 further comprising additional gas cells wherein each gas cell includes a transmitting and receiving unit for sending and receiving data signals and a computer and data storage unit with an antenna for receiving unit for sending and receiving data signals.

13. An apparatus for gas spectroscopy of a gas of interest, comprising:
    a gas minicell, said gas minicell including
    a first side,
    a second side, and
    an interior,
    wherein said second side is opposed to said first side and wherein said interior is between said first side and said second side,
    two first side mirrors positioned in said interior adjacent said first side,
    a second side mirror positioned in said interior adjacent said second side wherein said second side mirror is opposed to said two first side mirrors with said interior between said two first side mirrors and said second side mirror,
    a gas containment system for introducing the gas of interest into said interior,
    a light source that produces a light beam,
    a transmitting optical fiber or fibers connected to said gas minicell that receives said light beam from said light source and directs said light beam into said interior and onto the gas of interest in said interior,
    a receiving optical fiber or fibers connected to said gas minicell that receives said light beam from said gas of interest in said interior and directs said light beam from the gas of interest in said interior;
    wherein said two first side mirrors have inclinations that direct said light beam to said second side mirror and wherein said inclinations are offset to steer said light beam to completely fill said second side mirror and
    wherein said two first side mirrors and said second side mirror are positioned relative to each other and relative to said transmitting optical fiber or fibers and said receiving optical fiber or fibers that said light beam makes a multiplicity of different passes through said gas of interest in said interior, and a gas spectroscopy analyzer connected to said receiving optical fiber or fibers that receives said light beam from said receiving optical fiber or fibers and produces gas spectroscopy data.

14. The apparatus for gas spectroscopy of a gas of interest of claim 13 wherein said second side mirror has a notch that direct said light beam to said receiving optical fiber or fibers.

15. The apparatus for gas spectroscopy of a gas of interest of claim 13 wherein said two first side mirrors and said second side mirror are arranged to reflect said light beam so that said light beam makes a multiplicity of twenty seven different passes through the gas of interest in said interior.

16. The apparatus for gas spectroscopy of a gas of interest of claim 13 wherein said laser light source is a laser light source.

17. The apparatus for gas spectroscopy of a gas of interest of claim 16 wherein said laser light source is a tunable diode laser.

18. The apparatus for gas spectroscopy of a gas of interest of claim 16 wherein said laser light source is a multiplicity of individual lasers.

19. The apparatus for gas spectroscopy of a gas of interest of claim 16 wherein said laser light source is a tunable vertical cavity surface emitting laser for multiplexing by providing laser light with wavelengths for multiple gases of interest.

20. A method of analyzing a gas of interest, comprising the steps of:

providing a gas cell having a first side and a second side wherein said second side is opposed to said first side with an interior between said first side and said second side wherein the gas cell is a minicell having dimensions of four centimeters by five centimeters by one centimeter or less, positioning two first side mirrors in said interior adjacent said first side, positioning a second side mirror in said interior adjacent said second side wherein said second side mirror is opposed to said two first side mirrors with said interior between said two first side mirrors and said second side mirror, directing the gas of interest into said interior of said gas cell, using an emitting light source to produce a emission light beam, directing said emission light beam into said interior of said gas cell through an optical fiber to said two first side mirrors and to said second side mirror and onto the gas of interest, reflecting said emission light beam within said gas cell from said two first side mirrors through the gas of interest in said interior of said gas cell onto said second side mirror to make multiple different passes through the gas of interest, directing said emission light beam from said gas cell and from the gas of interest in said interior of said gas cell through an optical fiber to a spectroscopic analyzer, and using said spectroscopic analyzer to analyze said laser emission light to produce gas spectroscopy data.

21. The method of analyzing a gas of interest of claim 20 wherein said step of using an emitting light source to produce an emission light beam comprises using a tunable diode laser to produce a modulated emission laser light beam.

22. The method of analyzing a gas of interest of claim 20 wherein said step of using an emitting light source to produce an emission light beam comprises using a multiplicity of individual lasers produce an emission laser light beam.

23. The method of analyzing a gas of interest of claim 20 further comprising the step of providing a notch on said second side mirror and directing said emission light beam to said notch and from said notch to said optical fiber and to said spectroscopic analyzer.

* * * * *